United States Patent [19]
Dillon

[11] Patent Number: 5,980,923
[45] Date of Patent: *Nov. 9, 1999

[54] SEMI-INTERPENETRATING POLYMER NETWORK SCAR TREATMENT SHEETING, PROCESS OF MANUFACTURE AND USEFUL ARTICLES THEREOF

[75] Inventor: Mark E. Dillon, Huntingdon Valley, Pa.

[73] Assignee: Bio Med Sciences, Inc., Bethlehem, Pa.

[ * ] Notice: This patent is subject to a terminal disclaimer.

[21] Appl. No.: 08/910,304

[22] Filed: Aug. 11, 1997

Related U.S. Application Data

[63] Continuation of application No. 08/200,152, Feb. 23, 1994, Pat. No. 5,656,279.

[51] Int. Cl.$^6$ ........................................................ A61F 13/00
[52] U.S. Cl. ..................... 424/402; 424/443; 424/444; 424/445
[58] Field of Search .................... 424/402, 443, 424/444, 445

[56] References Cited

U.S. PATENT DOCUMENTS

| | | | |
|---|---|---|---|
| 4,832,009 | 5/1989 | Dillon | 128/156 |
| 4,945,125 | 7/1990 | Dillon et al. | 527/427 |
| 4,983,395 | 1/1991 | Chang et al. | 424/448 |
| 5,066,683 | 11/1991 | Dillon et al. | 424/448 |
| 5,157,058 | 10/1992 | Dillion et al. | 524/14 |
| 5,656,279 | 8/1997 | Dillion | 424/402 |

OTHER PUBLICATIONS

Sperling, *Interpenetrating Polymer Networks and Related Materials*, Plenum Press, New York, 1981, pp. 1–5.

Quinn, KJ, "Silicone Gel in Scar Treatment", *Burns*, 1987, 13, pp. 33–40.

Dillon, ME, Okunski, WJ, "Silon Non–Adherent Film Dressings on Autograft and Donor Sites", *Wounds*, 1992, vol. 4, No. 5:203–207.

Perkins, et al., Silocone Gel: A New Treatment for Burn Scars and Contracturers: Burns, 1982, 9, p. 201.

Dillon, ME, "Silicone and Poly(tetrafluoroethylen) Interpenetraiting Polymer Newtorks. Brief History, Summary of Recent . . . " *Interpenetraiting Polymer Networks* Klempner et al. Ed. ACS Books, New York, NY 1991, pp. 393–404.

*Primary Examiner*—Jyothsna Venkat
*Attorney, Agent, or Firm*—John F. A. Earley; John F. A. Earley, III; Harding, Earley, Follmer & Frailey

[57] ABSTRACT

Elastomeric sheeting materials are described which are formed from the process of (1) creating a membrane comprising a semi-interpenetrating polymer network ("IPN") of polytetrafluoroethylene ("PTFE") and polydimethylsiloxane ("PDMS") by causing a matrix of PDMS to be formed in situ with a matrix of PTFE; (2) causing a surface of substantially pure PDMS to be formed on at least one side thereof; (3) allowing said PDMS compositions to vulcanize; and (4) converting said structure into useful shapes suitable for application to anatomical areas of the body. The product of the process is suitable for the treatment of dermatologic scars, such as those associated with traumatic or surgical injuries of the skin. The pure PDMS layer provides desired therapeutic effects. The semi-IPN membrane provides improved physical integrity, durability, and elastic behavior in comparison to prior art. The combined structure has increased compliancy, a thinner profile, and improved patient comfort features in comparison to existing products.

17 Claims, 1 Drawing Sheet

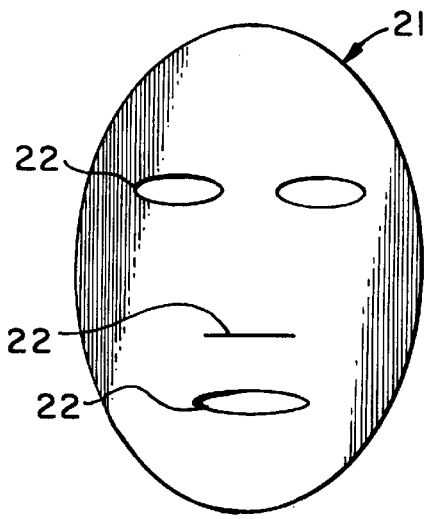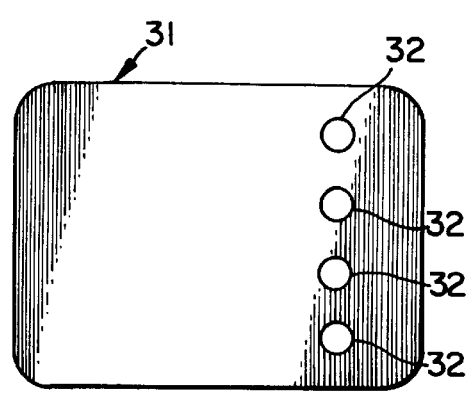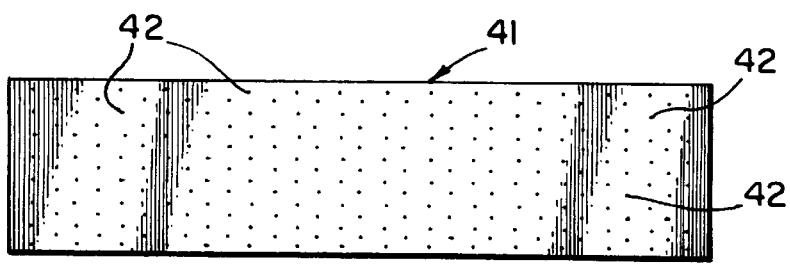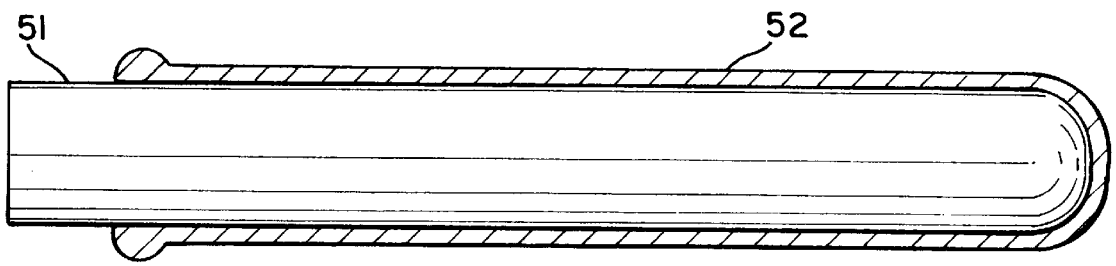

SEMI-INTERPENETRATING POLYMER NETWORK SCAR TREATMENT SHEETING, PROCESS OF MANUFACTURE AND USEFUL ARTICLES THEREOF

This is a continuation of application Ser. No. 08/200,152 filed on Feb. 23, 1994, now U.S. Pat. No. 5,656,279 issued on Aug. 12, 1997.

BACKGROUND OF THE INVENTION

1. Field of the invention

The present invention relates to the treatment of dermatologic scars, and more particularly concerns scar treatment sheeting and other articles, and a method of manufacture thereof.

2. Description of the Prior Art

Silicone chemistry has evolved since the early 1900's into a wide variety of systems used for industrial as well as medical applications. Medical grade silicones are usually based on thermoset dimethyl systems, whereby the molecular formula may be represented as follows:

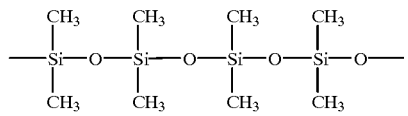

A crosslinking agent is used to create bonds between the hydrogen atoms on the methyl groups of adjacent molecules. These silicone formulations are often supplied as a two(2) part system, wherein one part contains a catalyst for vulcanization and the other part contains the base resin and crosslinking agent. By varying the amount of crosslinking agent, the crosslink density may be adjusted to achieve desired bulk or surface qualities of the vulcanized elastomer. Physical strength and durability tend to increase, while softness and coefficient of friction decrease with higher crosslink densities. Materials with a high crosslink density are relatively slick and tough, but have poor compliancy or "drapability". Silicones with low crosslink densities give a soft gel with a more adhesive or "tacky" surface. These materials are more drapable, although they are inherently weak and tend to fragment easily with low levels of stress.

A number of U.S. Patents and other publications relate to the field of the invention, and are as follows:

U.S. PATENT DOCUMENTS

| | | |
|---|---|---|
| 4,832,009 | 5/23/89 | Dillon |
| 4,945,125 | 7/31/90 | Dillon et al. |
| 5,066,683 | 11/19/91 | Dillon et al. |
| 5,157,058 | 10/20/92 | Dillon et al. |

OTHER PUBLICATIONS

Sperling, *Interpenetrating Polymer Networks and Related Materials,* Plenum Press, New York, 1981, pp. 1–5.

Dillon, M E, Okunski, W J, "Silon® Non-Adherent Film Dressings on Autograft and Donor Sites", *Wounds,* 1992, vol. 4, no. 5:203–207.

Dillon, M E, "Silicone and Poly(tetrafluoroethylene) Interpenetrating Polymer Networks: Brief History, Summary of Recent Developments, and Discussion of Applications", *Interpenetrating Polymer Networks,* Klempner et al. ed, ACS Books, New York, N.Y., 1991, pp. 393–404.

Perkins, et. al., "Silicone Gel: A New Treatment for Burn Scars and Contractures", *Burns,* 1982, 9, pp. 201.

Quinn, K J, "Silicone Gel in Scar Treatment", *Burns,* 1987, 13, pp. 33–40.

This invention relates to the treatment of dermatologic scars associated with traumatic or surgical injuries by using silicone elastomer materials. In many cases, scar formation may be excessive, resulting in raised, textured or colored surfaces. Scars can not only be disfiguring, but also limit range of motion and functionality. Historically, the application of pressure to an affected area of the body has been used to minimize these effects, particularly regarding hypertrophic and keloidal scars. Garments made of an elastic textile are used to achieve such pressure. This method of treatment eventually became a standard of care in many medical institutions, particularly burn treatment centers.

An Australian research group reported using silicone gel under pressure garments to evenly apply pressure in anatomic depressions, over areas of flexure, and during ambulation (Perkins et al., 1982). Quinn (1987) later found that the efficacy of silicone for scar modification was unrelated to pressure, in that the silicone material itself had a beneficial effect on the cosmetic appearance and elasticity of scars. The exact biological mechanism of this effect is not well understood.

In recent years, two (2) general types of silicone sheeting products have gained commercial acceptance in the marketplace for scar modification applications. One of the first types, Silastic® (Dow Corning Corporation) consists of a soft polydimethylsiloxane ("PDMS") gel material of approximately 0.125 inch (0.32 cm) in thickness. The low modulus of elasticity is beneficial by providing surface tack, thus promoting skin contact on difficult anatomical areas or during movement. The PDMS composition is inherently weak, however, and endures only several days in practice before breaking apart because of mechanical agitation. The above mentioned product uses a reinforcing scrim embedded into the body of the material to improve durability. This macroscopic mesh complicates the manufacturing process and may cause skin irritation if exposed during use. Although durability is increased, these products still disintegrate from normal wear and tear within a matter of weeks. This is a limiting factor in the cost effectiveness of the product in that the treatment may last for several months, thus requiring numerous repurchases. Together, the scrim and thickness of the product compromise drapability and comfort features.

The second type of commercial product, such as Sil-K® (Degania Silicone, Ltd.), consists of a relatively stiff silicone elastomer of approximately 0.03 inches (0.08 cm) in thickness. The increased modulus of elasticity provides for increased physical strength and durability, and the lack of a reinforcing scrim simplifies the manufacturing process. The material is relatively non-adherent, so adhesive tape is typically used to maintain the position of the material on the body. Although this material may last for the duration of treatment, it does not conform well to anatomical areas and does not provide a high level of patient comfort. This compromises patient compliancy and may limit the efficacy of the treatment.

Both types of products are relatively occlusive and impermeable to moisture vapor, which further detracts from patient comfort. There are other silicone-based scar treatment materials which have been commercialized, each generally falling into one of the two categories above. Some of the important properties of the above two examples of commercial products are listed in Table VII.

| Definitions | |
|---|---|
| Moisture Vapor Transmission Rate | The rate at which water vapor permeates through a material calculated gravimetrically and expressed in units of g/m²/day. The test conditions are 50% relative humidity, 98° F. (37° C.), with an air flow of 650 cubic feet per minute over the specimen. |
| Tensile Strength | The load required to break a test specimen divided by the cross-sectional area of the specimen. |
| Modulus of Elasticity | The tensile strength of a material at break divided by the elongation at break. |
| Coefficient of Friction | The force, measured in pounds, required to initiate the slide of a 1 inch square (6.45 cm²) by 0.5 inch (1.27 cm) thick piece of high density polyethylene over a test specimen on a horizontal surface. |
| Drapability | The distance the edge of a length of material bends when extended one inch beyond the surface of a ridged support with a corner radius of less than 1/16th inch. |

SUMMARY OF THE INVENTION

Interpenetrating polymer networks are defined as a blend of two or more polymers where each material forms a continuous network, each network interpenetrating the other (Sperling, 1981). An IPN is therefore a type of polymer/polymer composite. A true IPN comprises polymeric ingredients which are independently crosslinked. Systems wherein only one component is crosslinked are called semi-IPNs or pseudo-IPNs, such as an IPN of a linear thermoplastic polymer and a thermoset elastomer. For the purposes of this discussion, the terms IPN, semi-IPN, and pseudo-IPN shall be used interchangeably.

Because of the nature of composite materials, synergistic effects may be gained by carefully engineering the morphology and chemistry of the polymers in an IPN. My previous patents on this subject demonstrate increased strength may be gained without sacrificing other important properties, such as breathability. By using PDMS and polytetrafluoroethylene ("PTFE"), an IPN with a modulus of elasticity and surface chemistry substantially comprised of PDMS may be produced while also possessing the strength and durability of PTFE. The resultant material is semipermeable in that it allows moisture vapor transmission while preventing liquid water break-through. This technology has provided skin-like bandages and dressing materials for woundcare applications such as burn treatment (Dillon et al., 1992, FDA 510[k] approval no. K912032).

I have unexpectedly discovered that an IPN of PDMS and PTFE may be used as the basis of an elastomeric sheet useful for scar treatment applications. The subject of this invention allows the opposing properties of strength and softness in silicones elastomers to be simultaneously achieved; e.g. durability may be combined with drapability and surface tack. Furthermore, by causing one side of the structure to have a greater silicone content than the other, disparate surface properties may be imparted to each surface. The subject of the present invention represents an improvement over prior art in that the product:

1. is soft and compliant,
2. is strong and durable,
3. has a thinner profile,
4. has disparate surface properties on each side,
5. is moisture vapor permeable, and
6. has greater comfort features.

The manufacturing process lends itself to large-scale production in that continuous rolls of material may be made in virtually unlimited lengths. This provides for rapid and cost effective conversion into die-cut shapes or self-wound rolls.

BRIEF DESCRIPTION OF THE DRAWINGS

FIG. 1 is a view in cross section of a sheet constructed in accordance with this invention;

FIG. 2 is a view in top plan of a face mask constructed in accordance with this invention;

FIG. 3 is a view in top plan of a sheet which includes holes adapted for applying treatment to the webbed spaces between fingers or toes;

FIG. 4 shows a sheet which has perforations to facilitate the transfer of body heat through the sheet to thereby promote patient comfort; and FIG. 5 shows a view in section of a "finger cot" for application to the digits of the hand or other anatomical protrusions.

DETAILED DESCRIPTION OF THE DRAWINGS

Several embodiments of this invention are shown in the following illustrative examples and are not intended to be limiting. The following two-part silicone compositions were used in each example:

TABLE I

| Type: | Catalyst/ Resin Ratio | Description: |
|---|---|---|
| Silastic ® Silicone MDX4-4210 Dow Corning Corporation | 1:10 | High crosslink density, high modulus of elasticity, high tensile strength, low coefficient of friction |
| Silastic ® Silicone Q7-2218 Dow Corning Corporation | 1:1 | Low crosslink density, low modulus of elasticity, low tensile strength, high coefficient of friction |

EXAMPLE 1

The following blend of PDMS materials was prepared using trichloroethane as a processing aid:

TABLE II

| PDMS Material | Weight(g) | Percent |
|---|---|---|
| Q7-2218 Part A | 150.4 | 38.9 |
| Q7-2218 Part B | 150.4 | 38.9 |
| MDX4-4210Part B | 21.8 | 5.6 |
| Trichloroethane | 63.7 | 16.5 |

An IPN film of PDMS and PTFE was produced in the form of a continuous roll 12 inches (30 cm) wide according to the methods described in U.S. Pat. No. 4,945,125, the disclosures of which are incorporated herein by reference. Approximately 0.9 g of PTFE (Tetratec Corporation) was used per linear foot of IPN film produced. The IPN film was measured to have a thickness of 0.001 inches (0.0025 cm). The properties of this material are given in Table VII.

A second blend of PDMS materials was prepared as follows:

TABLE III

| PDMS Material | Weight(g) | Percent |
| --- | --- | --- |
| Q7-2218 Part A | 242.5 | 25.0 |
| Q7-2218 Part B | 242.5 | 25.0 |
| MDX4-4210 Part A | 440.9 | 45.5 |
| MDX4-4210 Part B | 44.1 | 4.5 |

A casting process was used to apply a 0.01 inch (0.025 cm) surface coating of the above PDMS composition to one side of the IPN film. The casting process involved passing the substrate through a reservoir of liquid PDMS prepolymer and using a doctoring roll to meter off a controlled amount of liquid as to leave a precise thickness of PDMS on the surface of the IPN substrate. Numerous other methods of achieving such a coating will be apparent to those skilled in the art. The coated material was passed through a tunnel style oven as to initiate the curing process, then post cured in a closed oven for 3 hours at 158° F. (70° C.) to achieve full vulcanization. FIG. 1 shows a sectional view of the construction of this example, with IPN layer 11 and PDMS coating 12. For comparative purposes, the same process was used to create 0.01 inch (0.025 cm) sheet of the same PDMS material without the bottom layer of IPN film. A paper release liner (H. P. Smith Company) was used as a temporary substrate from which the PDMS sheet was later removed. Some of the important physical characteristics of each material produced by this example are given in Table VII.

EXAMPLE 2

The following blend of PDMS materials was produced:

TABLE V

| PDMS Material | Weight(g) | Percent |
| --- | --- | --- |
| Q7-2218 Part A | 44.0 | 4.0 |
| Q7-2218 Part B | 44.0 | 4.0 |
| MDX4-4210Part A | 320.0 | 29.1 |
| MDX4-4210Part B | 32.0 | 2.9 |
| Trichloroethane | 660.0 | 60.0 |

An IPN film of PDMS and PTFE was produced in the form of a continuous roll 12 inches (30 cm) wide using the PDMS blend of Table V according to the methods previously described. Approximately 1.3 g of PTFE (Tetratec Corporation) was used per linear foot of IPN film produced. The final IPN was measured to have a thickness of 0.002 inches (0.05 cm).

A second blend of PDMS materials were prepared as follows:

TABLE VI

| PDMS Material | Weight(g) (g) | Percent |
| --- | --- | --- |
| Q7-2218 Part A | 232.5 | 25.0 |
| Q7-2218 Part B | 232.5 | 25.0 |

TABLE VI-continued

| PDMS Material | Weight(g) (g) | Percent |
| --- | --- | --- |
| MDX4-4210 Part A | 422.7 | 45.5 |
| MDX4-4210 Part B | 42.3 | 4.5 |

The process outlined above was used to apply a a 0.036 inch (0.091 cm) surface coating of the above PDMS blend to one side of the IPN film. As with the previous example, the material was passed through tunnel style oven as to initiate the curing process, then post-cured in a closed oven for 3 hours at 158° F. (70° C.). Again the same process was used to create 0.03 inch (0.075 cm) sheet of the same PDMS material without the bottom layer of IPN film. Some of the important physical characteristics of the materials produced by this example are given in Table VII.

The above samples are preferred embodiments of this invention. Other formulations and constructions will be apparent to those skilled in the art. For example, there are many other silicone compositions that would be suitable for the subject of this invention, either in combination or in blends. Dow Corning Silastic® grades MDX4-4515, Q7-2213, Q7-2167, Q7-2168, Q7-2174, Q7-2245, Q7-4840, and Q7-4850 are suitable substitutes. Furthermore, various thicknesses of IPN films and silicone coatings may be useful. The range of suitable IPN thickness is between 0.0005 inch (12.5 microns) and 0.02 inch (0.05 cm), and that for the PDMS is between 0.005 inch (0.0125 cm) and 0.25 inch (0.64 cm). An important consideration is that the final construction is not so thin as to have a tendency to wrinkle or otherwise be difficult to handle. The steps of creating a layered article may be reversed or even consolidated into one process.

In addition to various compositions, there are numerous shapes and sizes useful for the subject of this invention. For example, the invention may be converted into sheets or rolls for final use. Other embodiments include face-mask designs as shown in top plan view in FIG. 2 which shows a face mask 21 with cut openings 22 which accommodate the features of the face. An additional embodiment is shown in top plan view in FIG. 3, wherein a sheet 31 includes holes 32 cut as to apply treatment to the web-spaces between fingers and toes. Yet another embodiment is shown in FIG. 4 where a sheet 41 has perforations 42 to facilitate the transfer of body heat through the sheet 41, thereby promoting patient comfort.

A particularly novel configuration of this invention is a "finger cot" for application to the digits of the hand or other anatomical protrusions. FIG. 5 shows a sectional view of this embodiment and shows a mandrill 51 covered by an inventive article 52. This configuration may be achieved by: (1) conforming—or forming—a PTFE/PDMS IPN article around the end of a suitable mandrill, (2) dipping the mandrill in a reservoir of uncured polysiloxane, (3) removing the mandrill from the reservoir, (4) allowing the residual surface coating of polysiloxane to vulcanize, (5) removing the polysiloxane coated IPN article by peeling it off of the mandrill as it is turned in-side-out, and (6) (optionally) rolling the mouth of the shaped article outward and back to facilitate application by rolling the mouth of the product back down over the anatomical protrusion.

TABLE VII

| Specimen | Thickness Inch | Moisture Vapor Permeability g/m$^2$/24 hours | Tensile Strength[1] Lbs/in$^2$ | Modulus of Elasticity Lbs/in$^2$ | Drapability Inch | Coefficient of Friction (Side A/Side B)[2] Pounds |
|---|---|---|---|---|---|---|
| Silastic (Dow Corning) | 0.125 | 19.8 | 18.4 | 7.3 | 0.5 | 11.3/2.9 |
| Sil-K (Degania Silicone) | 0.032 | 41.3 | 981.4 | 101.4 | 0.34 | 0.5/0.5 |
| Example 1 IPN Film | 0.001 | 740.7 | 2638.5 | 1499.1 | 0.94 | 1.8/1.8 |
| Example 1 IPN w/PDMS Coating | 0.011 | 204.2 | 115.0 | 38.1 | 0.94 | 5.2/3.4 |
| Example 1 PDMS Sheet Only | 0.010 | 331.9 | 4.0 | 3.3 | 0.94 | 9.0/9.0 |
| Example 2 IPN Film | 0.002 | 770.0 | 2652.6 | 1020.2 | 0.94 | 1.1/1.1 |
| Example 2 IPN w/PDMS Coating | 0.038 | 51.9 | 55.5 | 18.8 | 0.88 | 13.9/3.6 |
| Example 2 PDMS Sheet Only | 0.030 | 99.3 | 6.3 | 4.8 | 0.94 | 9.0/9.0 |

[1]Tensile Tests were performed at a strain rate of 3.34 × 10$^{-2}$ in/sec. Note: the ultimate load required to break a one inch wide length of the specimens equals the tensile strength multiplied by the thickness.
[2]Side A is applied to the skin

What is claimed is:

1. A composite article for treating dermatological scars, comprising
    a first layer of a crosslinked elastomer, and
    a second layer of a membranous film,
    wherein the crosslinked elastomer is polydimethylsiloxane, and
    wherein said membranous film is a semi-interpenetrating polymer network of polydimethylsiloxane and polytetrafluoroethylene.

2. The article of claim 1,
    wherein each layer has surface characteristics that are disparate from the other layer.

3. The article of claim 1,
    with a moisture vapor transmission rate of at least 51.9 g/m$^2$/day.

4. The article of claim 1,
    with a drapability of at least 0.88 inches.

5. The article of claim 1,
    with a modulus of elasticity of less than or equal to 38.1 lbs/in$^2$.

6. The article of claim 1,
    wherein the layer of polydimethylsiloxane is 0.01 inches thick.

7. The article of claim 1,
    wherein the layer of polydimethylsiloxane is 0.03 inches thick.

8. The article of claim 1,
    wherein the semi-interpenetrating polymer network is 0.001 inches thick.

9. The article of claim 1,
    wherein the semi-interpenetrating polymer network is 0.002 inches thick.

10. A process which comprises the steps of
    (1) forming a membranous film,
    (2) causing a surface of polysiloxane to be formed on at least one side thereof to form a composite structure, and
    (3) converting said structure into shapes for application to anatomical areas of the body,
    wherein the membranous film is an interpenetrating polymer network of polysiloxane and polytetrafluoroethylene.

11. The process of claim 10, including
    applying said shapes to dermatologic scars.

12. The process of claim 11,
    wherein the shapes have holes to accommodate fingers, toes or other anatomical protrusions.

13. The process of claim 11,
    wherein the shapes are configured in a face-mask fashion.

14. The process of claim 11,
    wherein the shapes have perforations to promote heat transfer from the body.

15. The process of claim 11,
    wherein the shapes are configured in the fashion of a finger cot.

16. A process which comprises the steps of
    (1) forming a membranous film,
    (2) causing a surface of polysiloxane to be formed on at least one side thereof to form a composite structure, and
    (3) converting said structure into shapes for application to anatomical areas of the body,
    said membranous film being an interpenetrating polymer network of polysiloxane and polytetrafluoroethylene,
    said shapes having holes to accommodate figures, toes or other anatomical protrusions, and
    said shapes having perforations so as to promote heat transfer form the body.

17. The process of claim 16,
    wherein the shapes are configured in the fashion of a finger cot.

* * * * *